(12) United States Patent
Cinquin et al.

(10) Patent No.: US 9,649,169 B2
(45) Date of Patent: May 16, 2017

(54) SYSTEM AND METHOD FOR ANALYSING A SURGICAL OPERATION BY ENDOSCOPY

(75) Inventors: Philippe Cinquin, Nazaire les Eymes (FR); Sandrine Voros, Sevres (FR); Pierre Mozer, Vincennes (FR); Aurel Messas, Paris (FR); Jean-Alexandre Long, Bernin (FR); Alexandre Moreau-Gaudry, Grenoble (FR)

(73) Assignee: Universite Grenoble Alpes, Saint Martin d'Heres (FR)

( * ) Notice: Subject to any disclaimer, the term of this patent is extended or adjusted under 35 U.S.C. 154(b) by 1703 days.

(21) Appl. No.: 12/674,847

(22) PCT Filed: Aug. 20, 2008

(86) PCT No.: PCT/EP2008/060873
§ 371 (c)(1),
(2), (4) Date: Jun. 25, 2010

(87) PCT Pub. No.: WO2009/027279
PCT Pub. Date: Mar. 5, 2009

(65) Prior Publication Data
US 2011/0046476 A1    Feb. 24, 2011

(30) Foreign Application Priority Data
Aug. 24, 2007   (FR) .................................. 07 57161

(51) Int. Cl.
*A61B 34/10*   (2016.01)
*A61B 90/00*   (2016.01)
(Continued)

(52) U.S. Cl.
CPC ............. *A61B 34/10* (2016.02); *A61B 34/35* (2016.02); *A61B 90/36* (2016.02); *G09B 23/285* (2013.01);
(Continued)

(58) Field of Classification Search
CPC .... G09B 23/28; G09B 23/283; G09B 23/285; G09B 23/286; G09B 23/288; A61B 19/50;
(Continued)

(56) References Cited

U.S. PATENT DOCUMENTS

| 5,197,476 A | 3/1993 | Nowacki et al. |
| 5,494,041 A | 2/1996 | Wilk |

(Continued)

FOREIGN PATENT DOCUMENTS

| DE | 20321068 | 1/2006 |
| DE | 203 21 068 | 2/2006 |

(Continued)

OTHER PUBLICATIONS

Crow et al; "Assessment of Fiberoptic Near-Infrared Raman Spectroscopy for Diagnosis of Bladder and Prostate Cancer"; Adult Urology; Elsevier; 65; pp. 1126-1130, 2005.

(Continued)

*Primary Examiner* — Timothy A Musselman
(74) *Attorney, Agent, or Firm* — Harness, Dickey & Pierce, P.L.C.

(57) ABSTRACT

The invention concerns an analysis method for a surgical operation via endoscopy performed at an operative site in a volume located inside the body of an animal, characterized in that it comprises the steps consisting of:
  detecting at least one instrument (1; 2; 3) present at the operative site,
  detecting at least one portion of an organ (4) in the vicinity of the detected instrument (1; 2; 3),
  determining the positioning of the detected instrument (1; 2; 3) relative to the detected organ (4), so that the detected instrument (1; 2; 3), the detected portion of organ (4) and their relative positioning form parameters defining a detected surgical step, (Continued)

selecting, in a database, a conceptual surgical step corresponding to the detected surgical step from to the detected instrument (1; 2; 3), the detected portion of organ (4) and their relative positioning, comparing the parameters of the detected surgical step with the parameters defining the selected conceptual surgical step to determine the differences between these parameters, providing information on the quality of the detected surgical step on the basis of the determined differences.

24 Claims, 2 Drawing Sheets

(51) Int. Cl.
| | |
|---|---|
| *A61B 34/35* | (2016.01) |
| *G09B 23/28* | (2006.01) |
| *A61B 17/00* | (2006.01) |
| *A61B 18/00* | (2006.01) |
| *A61B 34/00* | (2016.01) |
| *A61B 34/20* | (2016.01) |

(52) U.S. Cl.
CPC ..... *A61B 34/20* (2016.02); *A61B 2017/00119* (2013.01); *A61B 2017/00128* (2013.01); *A61B 2017/00274* (2013.01); *A61B 2018/00547* (2013.01); *A61B 2034/252* (2016.02); *A61B 2034/256* (2016.02); *A61B 2090/08021* (2016.02); *A61B 2090/364* (2016.02); *A61B 2090/395* (2016.02); *A61B 2090/3941* (2016.02); *A61B 2090/3945* (2016.02)

(58) Field of Classification Search
CPC ......... A61B 19/52; A61B 19/54; A61B 34/10; A61B 34/20; A61B 2034/101; A61B 2034/102; A61B 2034/105; A61B 2034/107; A61B 2034/108
USPC .................................................. 434/262–275
See application file for complete search history.

(56) References Cited

U.S. PATENT DOCUMENTS

| | | | |
|---|---|---|---|
| 5,791,907 | A | 8/1998 | Ramshaw et al. |
| 5,882,206 | A | 3/1999 | Gillio |
| 6,134,539 | A | 10/2000 | O'Connor et al. |
| 6,875,886 | B2 | 4/2005 | Frangioni |
| 7,381,407 | B1 | 6/2008 | Murphy et al. |
| 9,055,881 | B2 * | 6/2015 | Gilboa ............... A61B 1/00128 |
| 2002/0155520 | A9 * | 10/2002 | Lichtman ............... G01N 33/50 435/40.5 |
| 2003/0198996 | A1 * | 10/2003 | Surber et al. .................. 435/7.1 |
| 2005/0145257 | A1 | 7/2005 | Barrera |
| 2005/0177400 | A1 * | 8/2005 | Rosenfeld et al. ............... 705/3 |
| 2006/0253107 | A1 | 11/2006 | Hashimshony et al. |
| 2007/0172803 | A1 * | 7/2007 | Hannaford et al. ........... 434/262 |
| 2009/0281839 | A1 * | 11/2009 | Lynn et al. ....................... 705/3 |
| 2011/0014596 | A1 * | 1/2011 | Kurenov ............... G09B 23/285 434/262 |

FOREIGN PATENT DOCUMENTS

| | | |
|---|---|---|
| EP | 1 080 695 | 3/2001 |
| EP | 1080695 | 3/2001 |
| EP | 1 649 822 | 4/2006 |
| EP | 1649822 | 4/2006 |
| FR | 650591 | 1/1929 |
| FR | 0757158 | 12/1933 |
| FR | 2 897 703 | 8/2007 |
| FR | 2 920 084 | 2/2009 |
| WO | 02/09571 | 2/2002 |

OTHER PUBLICATIONS

Krupa et al.; "Autonomous 3-D Positioning of Surgical Instruments in Robotized Laparoscopic Surgery Using Visual Servoing"; IEEE Transactions on Robotics and Automation, vol. 19, No. 5, pp. 842-853; Oct. 2003.

Berkelman et al.; "Automatic Instrument Tracking With a Compact Laparoscopic Endoscope Robot Using an External Optical Localizer"; pp. 77-82; 2002.

Wei et al.; "Real-Time Visual Servoing for Laparoscopic Surgery Controlling Robot Motion With Color Image Segmentation"; IEEE Engineering in Medicine and Biology; Jan./Feb. 1997; 16: pp. 40-45.

Casals et al.; "Automatic Guidance of an Assistance Robot in Laparoscopic Surgery"; International Conference on Robotics and Automation; Minneapolis, Minnesota; pp. 895-900; Apr. 1996.

Ko et al.; "Intelligent Interaction Between Surgeon and Laparoscopic Assistant Robot System"; IEEE International Workshop on Robots and Human Interactive Communication; pp. 60-65; 2005.

Doignon et al.; "Real-Time Segmentation of Surgical Instruments Inside the Abdominal Cavity Using a Joint Hue Saturation Color Feature"; Science Direct; Real-Time Imaging 11; 2005; pp. 429-442.

Herline et al.; Technical Advances Toward Interactive Image-Guided Laparoscopic Surgery; Surgical Endoscopy; Springer-Verlag; 2000; 14: 675-679; New York Inc.

Soler et al.; "Virtual Reality and Augmented Reality in Digestive Surgery"; IEEE Computer Society; pp. 278-279; 2004.

Aron et al.; "Preliminary Experience With the Niris TM Optical Coherence Tomography System During Laparoscopic and Robotic Prostatectomy"; Journal of Endourology; vol. 21; No. 8; pp. 814-818; Aug. 2007.

Fuchs et al.; "Augmented Reality Visualization for Laparoscopic Surgery"; Proceedings of Medical Image Computing and Computer Assisted Interventions (MICCAI); pp. 934-943, 1998.

Devernay et al.; "Towards Endoscopic Augmented Reality for Robotically Assisted Minimally Invasive Cardiac Surgery"; Proceedings of Medical Imaging and Augmented Reality; 2001.

Ukimuraa et al; "Adult Urology"; The Journal of Urology; vol. 175; Issue 4; pp. 1304-1310; Apr. 2006.

Lin et al.; "Automatic Detection and Segmentation of Robot-Assisted Surgical Motions"; Proceedings of MICCAI; Springer-Verlag Berlin Heidelberg; pp. 802-810, 2005.

Jannin et al.; "Modeling Surgical Procedures for Multimodal Image-Guided Neurosurgery". Springer-Verlag Berlin Heidelberg; MICCAI; 2003; pp. 565-572; 2208/2001.

Jannin et al.; "De La Neurochirurgie Guidee Par L'Image, Au Processus Neurochirurgical Assiste Par La Connaissance Et L'Information"; Habilitation a Diriger Des Recherches; Faculte De Medecine Universite De Rennes 1; Soutenue Le Oct. 14, 2005.

Mackenzie et al.; "Hierarchical Decomposition of Laparoscopic Surgery: A Human Factors Approach to Investigating the Operating Room Environment"; Min Invas Ther & Allied Technol; 10(3); pp. 121-127; 2001.

Ahmadi et al.; "Recovery of Surgical Workflow Without Explicit Models"; MICCAI, LNCS 4190; Springer-Verlag Verlia Heidelberg; pp. 420-428, 2006.

Padoy et al; "A Boosted Segmentation Method for Surgical Workflow Analysis"; MICCAI; Springer-Verlag Berlin Heidelberg; pp. 102-109; 2007.

Tang et al.; "Analysis of Errors Enacted by Surgical Trainees During Skills Trainees During Skills Training Courses"; Surgery; 2005; 138:14-20; Issue 1; http://www.surgjournal.com/article/piis003960600500228x/abstract.

Voros et al.; "Automatic Localization of Laparoscopic Instruments for the Visual Servoing of an Endoscopic Camera Holder"; 9th International Conference on Medical Image Computing and Computer Assisted Surgery (MICCAI 2006), LNCS 4190, pp. 535-542, Copenhague, Denmark, Oct. 2006.

(56) References Cited

OTHER PUBLICATIONS

International Search Report of PCT/EP2008/060873, completed Feb. 24, 2009.

* cited by examiner

SYSTEM AND METHOD FOR ANALYSING A SURGICAL OPERATION BY ENDOSCOPY

CROSS REFERENCE TO RELATED APPLICATIONS

This application is a National Phase of PCT/EP2008/060873 filed Aug. 20, 2008, which claims priority to FR 0757161 filed Aug. 24, 2007.

BACKGROUND OF THE INVENTION

Field of the Invention

The present invention relates to the field of endoscopic surgery, and more precisely the methods and systems used to assist the practitioner in these surgical operations.

State of the Art

Endoscopic surgery requires the visualization of anatomical structures depicted in non-usual manner along a viewing axis that is different from the one used in conventional open surgery. In particular, the image is very often in two dimensions only, and the image is magnified which means that reference marks are modified, etc. In addition, control over instruments is often the reverse of their real movement in space, which imposes additional factors to be taken into account by the practitioner, compared with open surgery.

On this account, the performing of endoscopic operations requires specific learning, combining a procedural learning component, i.e. relating to hand coordination, with a visual learning component i.e. relating to coordination between actual procedure and the patient. This learning is necessary both for a practitioner with no particular surgical experience, and for a surgeon qualified in conventional open surgery but who has no experience in endoscopic surgery. This is notably the case for the learning of laparoscopic surgery as compared with laparotomy.

This learning is long and complex. First, a theoretical learning phase is required to learn to integrate the theoretical positioning of the instruments with respect to the organs, in relation to the surgical task to be performed. The different surgery protocols corresponding to different surgical operations must also be learnt. A surgery protocol is defined as a succession of surgical steps for the purpose of carrying out the corresponding surgical operation. A surgical step comprises one or more elementary surgical tasks conducted in a region of an operative site to obtain the surgical result corresponding to one of the steps in performing the surgical operation.

The second phase is the practical learning phase. This consists of becoming familiar with the endoscopic approach to surgery i.e. manipulating instruments under endoscopic guidance. This second learning phase is generally carried out on a human cadaver or an animal.

To overcome the length and complexity of this learning, solutions have been developed in an attempt to reduce the learning curve for practitioners so that they may soon become operational.

U.S. Pat. No. 5,791,907 can be cited which proposes a learning device for training in surgery protocols for surgical operations including under endoscopy. This device comprises a screen which displays a partial sequence of a surgical procedure i.e. a succession of surgical steps; once this sequence has been viewed, the user must input data to characterize the following surgical step in the procedure, by indicating for example which instrument is to be used, in which position, etc. Nonetheless, said device does not provide for improvement in the practical learning phase which is the most complex and above all the longest.

To improve this practical learning phase, simulators have been proposed to place the practitioner under real conditions. These simulation devices are of interest since they can shorten the learning step on cadavers or animals. However, they do not truly bring acceleration of the practitioner's practical learning phase.

Despite these new learning tools, learning will never be perfect. Practitioners gain much more experience during their first real operations under endoscopy. It is estimated for example that a surgeon must operate on a hundred or so patients before being fully efficient for a radical prostatectomy via endoscopic route. This implies that the practitioner may make surgical errors during initial operations. These errors may have consequences such that it is necessary to complete the operation under open surgery, which has consequences for the patient and for the hospital. In addition, this may lead to less effective management of the disease (higher percentages of margins of resection during the learning period, longer operating times, increased morbidity rates) which has functional and carcinological consequences for the patient, and also financial consequences not only for the hospital but also more generally for society as a whole.

One purpose of the present invention is to propose an analysis method and system for surgical operations via endoscopy with which to solve at least one of the above-cited disadvantages.

In particular, one purpose of the present invention is to propose a method and system allowing a practitioner to rectify any errors during a surgical operation before there are any irreversible consequences for the endoscopic operation in progress.

Another purpose of the present invention is to propose a method and system offering practitioners the possibility to analyze retrospectively the conducting of any of their surgical operations via endoscopy.

DISCLOSURE OF THE INVENTION

For this purpose, an analysis method is proposed for a surgical operation under endoscopy performed at an operative site in a volume located inside the body of an animal, characterized in that it comprises the steps consisting of:
 detecting at least one instrument present at the operative site,
 detecting at least one portion of an organ in the vicinity of the detected instrument,
 determining the positioning of the detected instrument relative to the detected organ, so that the detected instrument, the detected portion of organ and their relative positioning form parameters defining a detected surgical step,
 selecting, in a database, a conceptual surgical step corresponding to the detected surgical step in relation to the detected instrument, to the detected portion of organ and to their relative positioning,
 comparing the parameters of the detected surgical step with the parameters defining the selected conceptual surgical step to determine the differences between these parameters,
 providing information on the quality of the detected surgical step on the basis of the determined differences.

Preferred, but non-limiting, aspects of this analysis method are the following:

the method is applied during the surgical operation to provide assistance in real time;

the method is applied after the surgical operation to allow retrospective analysis of the surgical operation performed;

the parameters of the detected surgical step are also compared with the parameters of past performed surgical steps derived from previous surgical operations and stored in the database with the conceptual surgical steps, this comparison being intended to fine-tune the differences ascertained with past performed surgical step(s) in order to provide more precise information on the quality of the detected surgical step;

the method further comprises a step consisting of selecting a surgery protocol in the database, a surgery protocol being a succession of surgical steps for the conducting of a surgical operation, the selected surgery protocol corresponding to the surgical operation performed and to a succession of detected surgical steps;

the surgery protocol is also selected in relation to parameters characteristic of the animal and which may have an impact on the conducting of the surgical operation;

the information on quality comprises a depiction of the required position of the instrument relative to the portion of organ according to the selected conceptual surgical step and the selected surgery protocol;

the information on quality comprises a depiction of the instrument as an overlay over an image of the operative site showing the required position of the instrument relative to the portion of organ;

the method further comprises a step consisting of selecting in the database the past performed surgical step which, in the selected surgery protocol, follows after the detected surgical step, and in that it comprises the display of a depiction of said succeeding past performed surgical step;

the additional information comprises the triggering of an alert in the event that the last detected surgical step does not allow the selection of a conceptual surgical step corresponding to the surgical operation performed and to the succession of prior surgical steps;

an endoscopic imaging technique is used for detection of the instrument and/or detection of the portion of organ;

for detection of the portion of organ, a labelling substance is used to label said organ, said substance containing a fluorescent substance and antibodies specific to the organ, the endoscopic camera being adapted for the band of fluorescence wavelengths of the labelling substance.

An analysis system is also proposed for a surgical operation via endoscopy performed at an operative site in a volume located inside the body of an animal, comprising:

a database in which conceptual surgical steps are stored, means to detect at least one instrument present at the operative site, means to detect at least one organ 4 in the vicinity of the detected instrument, means to determine the positioning of the detected instrument relative to the detected organ, means to select, in the database, a conceptual surgical step corresponding to a detected surgical step in relation to the detected instrument, to the detected organ and their relative positioning, means to compare the parameters of the detected surgical step with the parameters defining the selected conceptual surgical step, and means to determine the differences between these parameters, means to provide information on the quality of the detected surgical step on the basis of the determined differences.

Preferred but non-limiting aspects of this analysis system are the following:

the database comprises means to store surgery protocols, a surgery protocol being a succession of surgical steps, for the performing of a surgical operation, the system further comprising means to select, in the database, a surgery protocol corresponding to the surgical operation performed and to a succession of detected surgical steps;

the means to provide information on quality comprise means to indicate the required position of the instrument relative to the portion of organ according to the selected conceptual surgical step and the selected surgery protocol;

the means to provide information on quality further comprise means to display a depiction of the instrument as an overlay over an image of the operative site showing the required position of the instrument relative to the portion of organ;

the system further comprises means to select, in the database, the past performed surgical step which, in the selected surgery protocol, follows after the detected surgical step, and in that the means to provide information on quality further comprise means to display a depiction of said succeeding past performed surgical step;

the means to provide additional information comprise means to trigger an alert in the event that the last detected surgical step does not allow selection of a conceptual surgical step corresponding to the surgical operation performed and to the succession of previous surgical steps.

BRIEF DESCRIPTION OF THE FIGURES

Other characteristics and advantages will become further apparent from the following description which is solely illustrative and is non-limiting, to be read with reference to the appended figures amongst which.

DETAILED DESCRIPTION OF THE INVENTION

As indicated above, a surgical operation corresponds to at least one surgery protocol, a surgery protocol being defined as a succession of surgical steps.

A surgery protocol can therefore be broken down into a succession of surgical steps for the performing of a particular surgical operation. Each surgical step can be described as a set of characteristics or parameters needed to obtain the corresponding specific surgical result. Therefore, a surgical step can be characterized for example by the use of a well defined set of surgical instruments in a precise region of the operative site, with a view to obtaining a specific surgical result (haemostasis, resection, suture, cleansing, etc.).

Therefore, for example in terms of surgical instruments, there will be two needle holders for the "suture" surgical step, bipolar forceps or scissors or ultrasound scalpel for the "resection" surgical step, or grasping pincers and a suction device for the "cleansing of the operative site" surgical step. The organs surrounding the instruments in the operative site are also indices used to determine which specific surgical step is to be conducted, at which organ, which provides additional information for the precise determination of a surgical step. This will be all the more precise if the relative positioning of the instruments relative to the organ is known.

Additionally, to determine to which surgical step the combined information on instrument, organ and their relative positioning may correspond, it may be helpful to know the preceding surgical steps in the surgery protocol under consideration. For example, the resection of the neck of the bladder will always comprise a resection step followed by a cleansing step since, at the step to open the neck of the bladder, it is known that urine arrives in the operative site which must be removed.

Therefore, for each surgical result to be achieved, a category or class of surgical step can be defined called a "conceptual surgical step" which corresponds to a conceptual description of what is to be carried out to obtain the desired surgical result, this conceptual description being substantiated by precise parameters defining the surgical step.

Similarly, "conceptual surgery protocols" can be defined which also correspond to categories or classes of surgery protocols defined by a certain number of parameters.

The notions of surgery protocol and surgical step also apply to describe particular instantiations of their conceptual parallel: in this case, the terms "past performed surgery protocol" or "past performed surgical step" will be used if the corresponding concepts were implemented in a particular patient, by a given surgical team at a precise time and in a precise place. Past performed surgery protocols and past performed surgical steps therefore form data derived from prior surgical operations defined on the basis of a certain number of characteristic parameters. These parameters are used in particular to specify to which conceptual surgery protocol, or to which conceptual surgical step, the said past performed surgery protocol or the said past performed surgical step may correspond.

When these past performed surgery protocols or past performed surgical steps conform to "recipes" or to "recommendations" and allow a result to be obtained which conforms to the current state of surgical knowledge, the terms "recommended past performed surgery protocol" or "recommended past performed surgical step" will be used. It may also be helpful, in particular for the purpose of teaching or for detailed evaluation of the quality of surgery, also to define "incorrect past performed surgery protocols", or "incorrect past performed surgical steps", which correspond for example to past performed surgery protocols or past performed surgical steps with characteristic parameters removed from the theoretical parameters defined by the corresponding conceptual surgery protocol or conceptual surgical step, or even which correspond to situations in which the surgical operation encountered extensive complications.

An observer who uses any means, in particular video means or tracking means to record the relative position of organs and surgical instruments, has the possibility for example to compare a surgical step in progress with a conceptual surgical step, and optionally with past performed surgical steps corresponding to the conceptual surgical step, these conceptual surgical steps possibly being defined as recommended or incorrect. With the succession of surgical steps in progress, the surgery protocol in progress can be deduced and also compared with the corresponding conceptual surgery protocol.

The comparison of surgical steps in progress with conceptual and past performed surgical steps not only allows qualitative information to be obtained on the surgery being performed, but also quantitative information if this is expedient (for example by comparing instrument speeds, their positions relative to each other or relative to organs during the surgical step in progress with the speeds or relative positions between instruments or instruments and organs during the selected conceptual surgical step, even during a past performed satisfactory or unsatisfactory surgical step).

Each surgical operation can therefore be subdivided into a succession of surgical steps.

By filming the operative site during a past performed surgical operation, it is possible to obtain a video illustrating a complete past performed surgical procedure. This video can be viewed and subdivided into a succession of video sequences even a succession of images. Each video sequence or each image can then be examined to determine to which conceptual surgical step it corresponds. This may be carried out by processing the computer image in relation to the elements detected in the image under consideration, notably detected instruments, detected organs and their relative positioning. The order in which the different instruments are combined and are successively used at the operative site may also give an indication on the surgical step in progress. It is also possible to have recourse to the practitioner's theoretical and practical knowledge to determine to which conceptual surgical step the processed image corresponds.

Databases are known which group together videos showing surgical procedures conducted under ideal conditions, without any complications. These videos permit the defining of different past performed surgery protocols which are recommended for a particular surgical operation.

As is well known, it is through analysis of errors that the most efficient learning is achieved. This is why it is proposed also to analyze videos illustrating surgical operations during which errors were committed. These videos include procedures during which the errors were able to be corrected during the operation, so that the surgical operation was successfully completed, but also videos during which errors were not able to be corrected for which the consequences may have been more serious for the endoscopic operation in progress, possibly leading to a complication or conversion to open surgery. These videos can be used to define different past performed surgery protocols which were incorrect for the conducting of a particular surgical operation.

The analysis of all these videos allows different past performed surgery protocols to be obtained for one same surgical operation, these past performed surgery protocols being referenced and stored as recommended past performed surgery protocols or as incorrect past performed surgery protocols. This also permits each surgical operation to be broken down into a plurality of surgical steps, it also being sought to classify these in relation to conceptual surgical steps. All this data can then be grouped together in a suitable database. This database comprises firstly conceptual surgery protocols and surgical steps, and secondly past performed surgery protocols and surgical steps, optionally respectively classified as recommended or incorrect past performed surgery protocols and surgical steps.

Said database may in particular be useful during a theoretical learning phase, the user being able to learn not only so-called recommended surgery procedures, but also so-called incorrect surgery procedures which give information on action to be avoided. This also provides an opportunity to compare events which occurred during a given surgical step in different patients so as to facilitate learning by setting targets for the acquisition of knowledge for a given surgical step.

To improve surgeon training, and to provide assistance during operations under endoscopy, we propose using the data from this database following the procedure which will now be described in detail.

The described database can be used to store not only conceptual surgery protocols and surgical steps, but also a multitude of different past performed surgery protocols and surgical steps together with a certain amount of characteristic data. Each past performed surgical step is related to a particular conceptual surgical step but also to a particular surgical operation, to the notion of success or not of this surgical operation, to a particular past performed surgery protocol (making it possible to relate the surgical step with previous or subsequent surgical steps), etc.

We propose using this data to provide practitioners with information during a surgical operation, the primary objective of this information being to provide the practitioner and/or a third party supervising the operation, with an indication on the quality of surgery being performed or is to be performed, for example an indication on conformity with known recommendations for the surgical operation under consideration, or on the contrary on closeness to a known error. This information can also be used for retrospective analysis of the surgical operation performed by a surgeon.

For this purpose, it would be helpful to be able to detect at which conceptual surgical step the practitioner has arrived at, at a given moment, from the surgical step in progress. Once the conceptual surgical step has been selected, the surgical step in progress can be compared with the characteristics of the corresponding conceptual surgical step to measure possible differences and discrepancies with parameters defining the conceptual surgical step, in order to obtain a first level of information on the quality of surgery to achieve the desired surgical result, and on subsequent conducting of the surgical procedure in progress. This information on the quality of surgery is qualitative i.e. it relates to the conformity or non-conformity of the surgery being performed, but it may also be quantitative by giving specific values of differences or recommendations. It is also possible to compare the surgical step in progress with past performed surgical steps (whether recommended or incorrect) stored in the database, to obtain a second more fine-tuned level of information on the quality the surgery being performed, this information also being qualitative and quantitative.

Figure 1:
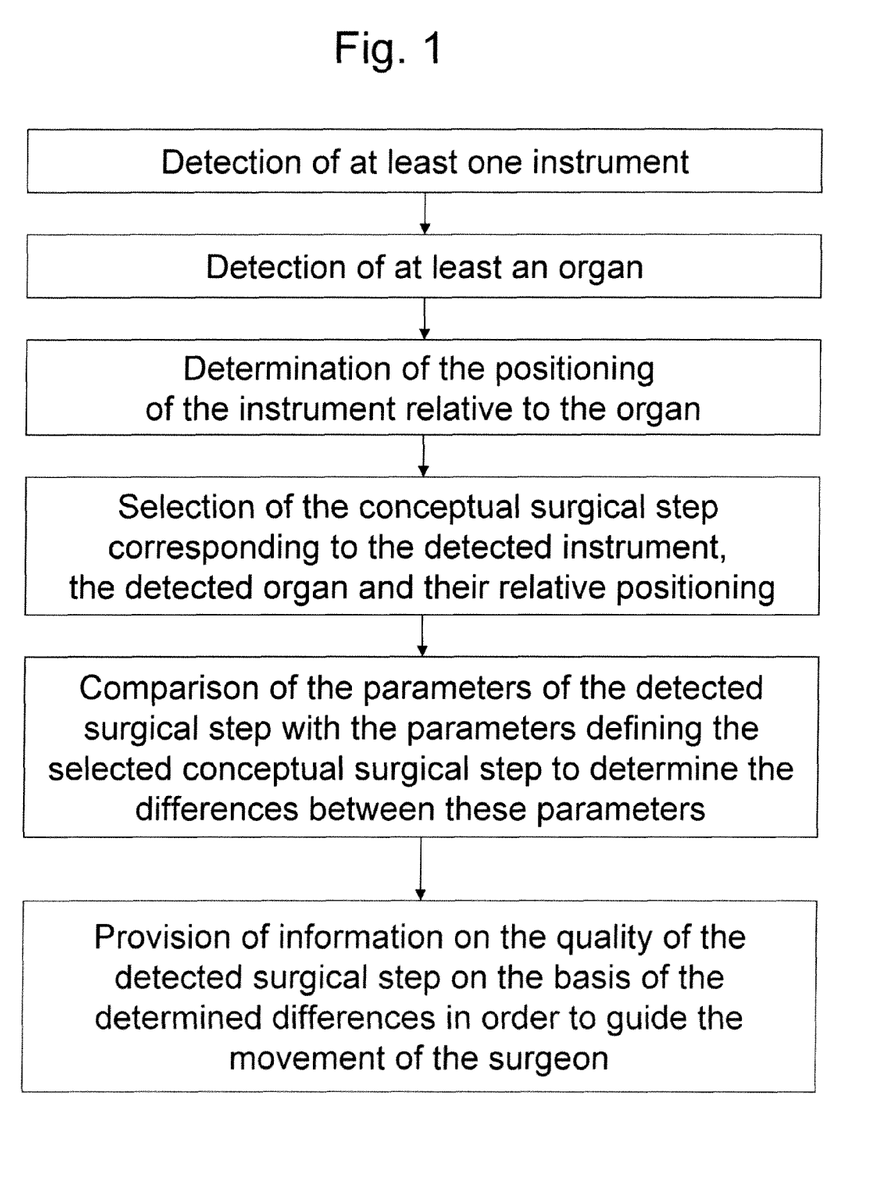
FIG. 1 is a diagram illustrating the method to analyse operative procedure during an endoscopic surgical operation.

The analysis method enabling surgeons to adapt surgery during an endoscopic procedure is schematically illustrated in FIG. 1.

As indicated above, a conceptual surgical step can be defined in relation to a certain number of parameters, such as in relation to the instrument(s) present in the operative site, in relation to the organ(s) also present in the operative site, or at least to portions of organs present in the operative site, and in relation to the relative positioning of these surgical instruments in relation to the organs or portions of organs. Therefore, these parameters need to be evaluated for the surgical step in progress so that they can be compared with parameters defining the conceptual surgical step.

The system according to the invention is therefore adapted to detect, at the operative site, both instruments and organs and to determine their relative positioning. It is possible to use any type of detection means. By detection is meant not only detection of the presence of instruments or organs but also their location and position in space.

Routinely, endoscopic cameras are used inserted via trocars into the cavity formed in the volume of interest so that it is possible to monitor the progress of procedure at the operative site.

The detection of instruments in the operative site can therefore be made using endoscopic images. Several methods exist to monitor and detect surgical instruments in a cavity via endoscopic route, which can be divided into several classes.

First there are methods based on the use of design of ad hoc devices permitting the locating of instruments and organs. An external optic locator is used which allows precise determination of the position and movement of the instruments in relation to the organs (see for example the publication by P. Berkelman, E. Boidard, and P. Cinquin, titled "Automatic instrument tracking with a compact laparoscopic endoscope robot using an external optical localizer", Proceedings of Surgetica, p. 17-24, 2002). With this type of approach, it is possible to overcome difficulties related to the use of images, but it makes surgical procedure more complex which already has recourse to numerous items of equipment.

Other methods are based on the adding of colour labels to instruments to simplify their detection in endoscopic images (see for example the publication by A. Casals, J. Amat, and E. Laporte, titled "Automatic Guidance of an Assistant Robot in Laparoscopic Surgery", Proceedings of the IEEE International Conference on Robotics and Automation, p. 895-900, 1996). However, this method can raise problems of sterilisation and the detection of several instruments is difficult.

More recently, a method based on image processing techniques has been developed.

According to this approach, the measurement is made of the three-dimensional (3D) positions of the instrument insertion points into the cavity of interest, and a simplified model of the shape of the instrument used. With suitable image processing, it is possible to monitor the position and movement of the instrument at the operative site. For a more complete description of this instrument detection method, reference can be made to French patent application n° 06-50591 filed on 20 Feb. 2006 with the title "Détection automatique d'un outil chirurgical sur une image fournie par un système d'imagerie medical" (Automatic detection of a surgical instrument in an image provided by a medical imaging system).

Evidently, other methods exist to detect instruments in endoscopic images, which may also be used.

Several approaches can also be used to detect organs or portions of organs at the operative site.

Here again, it is possible for example to use data provided by endoscopic cameras, even if any other acquisition means can be envisaged (such as an ultrasonic probe for example).

The sole information given by the endoscopic camera could be sufficient, but it is generally preferable to make provision in addition for means to enhance some organs of interest, so as to obtain a maximum amount of information for subsequent selection of the conceptual surgical step, and for comparison between the surgical step in progress and recommended or incorrect past performed surgical steps.

One solution may consist of using pre-operative images (in particular images acquired by CT scan, Magnetic Resonance Imaging or ultrasound) compared with images acquired by endoscope, so as to relate some organs by their shape, their relative position, etc.

It is also possible more simply, to use a database comprising models representing organs so that they can be recognized in automated fashion, by image processing, in images acquired per-operatively i.e. during the surgical operation. During the operation, a portion of the surface of the organ is acquired by a 3D feeler for example (generally a surgical instrument located in the space by an optic locator), then the model the closest to the real organ is searched in the database.

Evidently other methods exist to detect organs in endoscopic images which may also be used.

A particular method is described below which can be used to facilitate organ detection or the detection of a portion of an organ.

The principle of this method is to couple the organ, which it is more particularly desired to visualize, with means emitting a signal which can be recognized by the imaging device used.

One simple solution is to use a passive emitting device i.e. which can increase the contrast of the organ to be viewed solely by interaction between the emitting device and a particular light source.

To do so, it is possible for example to use a fluorescent labelling substance intended to be applied to the organ. In this case, the imaging device used is adapted to recognize the emitted fluorescent signal. For example, an endoscopic camera can be used, adapted for the band of fluorescence wavelengths.

Preferably, the labelling substance contains a fluorescent substance such as fluorescein, and antibodies specific to the organ. On this account, only the organ of interest will integrate the fluorescent substance under the action of the antibodies. This labelling substance is either injected directly into the operative site or it is distributed on the surface of the organ of interest.

To highlight the prostate in a radical prostatectomy operation for example, it is possible to use fluorescein labelled with anti-prostate antibodies (for example anti Prostate Specific Antigen or anti Prostate Specific Membrane Antigen (PSMA), such as Prostascint®).

Different antigens are targeted by the anti-prostate antibodies. With regard to Prostascint®, the target antigen is an epitope of the intracellular PSMA domain (type II transmembrane glycoprotein of the constituent cells of the prostate glandular epithelium). Evidently, other epitopes of this glycoprotein, in particular extracellular epitopes, can be targeted. For example BZL Biologics is currently working on the development and marketing of antibodies specific to an epitope of the extracellular domain of PSMA (monoclonal antibody "J591"). Initial clinical trials in man have already been conducted. One of the advantages of targeting epitopes in the extracellular domain is that this facilitates the identification of living cells, specific to the target tissue, these epitopes being directly "accessible" by the antibodies (no need to internalize the antibody in the cell).

Other antibodies of the PSMA extracellular domain can evidently be envisaged. For example, U.S. Pat. No. 7,381, 407 B1 of 3 Jun. 2008 to Gerald P. Murphy et al. reports on the identification and development of the antibody 3F5.4G6, specific to the PSMA extracellular domain. This antibody has been shown to be capable of binding to living tumour cells of the prostate. This antibody also has the particularity of targeting antigens of the extracellular domain of the PSM' protein, a variant of the PSMA protein identified during the invention described by the team led by Gerald P. Murphy and expressed by prostate cells (malignant or healthy).

Contrary to PSMA, PSM' is characterized in particular by the absence of any intracellular domain.

Therefore, under this invention, different antibodies or compatible associations and/or mixtures of antibodies labelled with a fluorophore (fluorescein type) and specific to prostate tissue can be used. These antibodies can be determined by the person skilled in the art, who may choose those in the catalogues of the different manufacturers of antibodies which are most suitable in relation to their sensitivity and ability to bind to target epitopes. For the labelling of fluorescein (or other fluorophore) with these antibodies, routine methods are currently used by the person skilled in the art.

By applying this substance to the prostate bed, it is possible after ablation of the prostate, to wash the bed (removal of excess labelled fluorophores that did not bind), to illuminate the bed in the wavelength of fluorescein excitation, to see whether any fluorescein remains, in which case this means that there is a "positive margin of resection". It is important to specify in this invention that in this descriptive step only the "organic" aspect of margins of resection is given consideration. In other words, a margin of resection is said to be "positive" if there subsist prostate cells in the margin whether benign (healthy) or malignant (pathological), a margin ideally being free of any prostate cells in particular glandular prostate cells ("negative margins"). Fluorescein has the advantage of being fully biocompatible. The antibodies are evidently also chosen to be biocompatible. By applying the labelling substance to the prostate bed, it is possible to overcome the fact that the excitation and emission wavelengths of fluorescein do not lie in the "transparency window" of biological tissues to light; it is effectively not a hindrance since observation is surface observation.

It is also possible to inject fluorescein labelled with antiprostate antibodies before the operation, for example by vein puncture. By means of the antibodies, the labelling substance only binds to the prostate tissues. Since the light emitted by fluorescein is absorbed by a few millimeters of tissue, fluorescence will only be seen to appear when surgical resection has exposed the prostate. This may also be used to detect positive margins.

Similarly, the visualization of the nerve structures of the neurovascular bundles can be achieved through the pre-operative injection of fluoroscein labelled with anti-nervous system antibodies. As previously, the identification is preferably made of antibodies specific to extracellular epitopes, to facilitate their binding to the tissue targets.

It is noted that in all these examples, there is no need to use a fluorophore capable of emitting in the transparency window of biological tissues (on the contrary, use is made of the fact that the light emitted by the fluorescein is very quickly absorbed by the tissues). It is an advantage of importance since the fluorophores capable of emitting in this wavelength are very few and have yet to prove that their biocompatibility is as good as that of fluorescein.

Another solution consists of using an active emitting device i.e. which emits a detectable energy directly using an additional energy source (typically a microbattery or rechargeable microbattery).

For example, a light source can be used positioned on the organ of interest, even inside the organ of interest. The use of a light source has the advantage that it can specifically identify an organ of interest directly in images derived from the endoscopic camera, without necessarily having to use a dedicated imaging device.

If the light source is intended to be inserted inside the organ (for example if a probe is inserted in the rectum, urethra, ureter or any other organ directly accessible by natural routes, or if necessary by percutaneous puncture) the light source is adapted to emit a light signal in the transparency window of biological tissues. The light signal is then emitted at a wavelength preferably of between 750 nm and 1350 nm. A suitable optic device can make this light source a point source. At least two cameras sensitive to the emitted wavelength should be positioned in the operative site. The size of these cameras must be such that they can be inserted via trocars, which is possible with cameras having CMOS technology for example. The relative position of these two cameras must be known, which can be obtained for example by means of a mechanical device and prior calibration. The very strong diffusion of light through the biological tissues makes detection of the light source projection in each camera more difficult. However, light diffusion models can be used to determine the position of the projected light source with sufficient accuracy, by processing the observed image. To do so, the distance between the light source and the surface observed by the cameras must not exceed a few centimeters. Interesting examples of such a situation are afforded by the urethra, neck of the bladder or base of the bladder. These are very important regions to locate in some steps of radical prostatectomy. Yet, during these steps they are located only a few centimeters away from the surface observed by the endoscopic cameras. This brings us to the situation of a conventional optic 3D locator, with the advantage however that it is acceptable for a biological tissue to lie between the light source and the cameras and also with the advantage that the cameras used can be inserted via trocars into the operative site. It is to be noted that it is possible to use several light sources (which may emit in turn) for example to locate all the three previously mentioned regions: urethra, neck of the bladder, base of the bladder. All that is required is to use a bladder probe comprising several optic fibres whose orifices lie at various distances from the tip of the probe.

An ultrasound source may also be used. Probes may be used which are designed to be inserted into organs directly accessible via natural routes (rectum, urethra, bladder, ureter, etc.) or probes attached to the tips of puncture needles (through the skin or through other organs). In this case, provision should be made for an ultrasound imaging device. The ultrasound source may be a piezoelectric transducer, a capacitive micromachined ultrasonic transducer (CMUT). The latter is of particular interest through the possible miniaturization of the probe, especially if the probe is to be inserted via puncture.

If an ultrasound source is used that is detected by an ultrasound imaging device, a cross-mapping system can be used between the endoscopic and ultrasound imaging means that is adapted for the synthesis of an enhanced image of the region of interest at the operative site, as is described below.

On the basis of data derived from detection of the instrument and detection of the organ, it is possible to determine their relative positions with respect to each other so as to complete information needed to determine the conceptual surgical step corresponding to the surgical step in progress, and for their subsequent comparison.

Any image processing means can be used, able to compute this relative positioning directly from the endoscopic image showing the instrument and the organ.

As indicated, if the imaging means used to detect the instrument and to detect organ are different means, a system is used that is adapted to relate and merge said images so that the relative position can also be determined by simple image processing.

The use of an ultrasound imaging device effectively allows ultrasound data to be obtained on the operative site, this data being very useful to visualize the organs, in particular those hidden in the endoscopic images of the endoscopic camera. It is further advantageous if an ultrasound source is used specifically to locate an organ of interest.

To facilitate merging of the endoscopic and ultrasound data for the purpose of synthesizing an enhanced image of the region of interest in the operative site, it is possible for example to use a set of markers arranged in the operative site, these markers being adapted so that they can be seen both by the endoscopic camera and by the ultrasound imaging device.

The markers used are preferably of small size so that they can easily be inserted into the cavity and positioned in the operative site. They may be separate from one another or they may be coupled to form a more or less rigid assembly. The only important point is that the markers must be fixed relative to one another at least during the acquisition of an endoscopic or ultrasound image.

So that they can be visible by the ultrasound imaging device, each marker may for example integrate an energy source powering a transducer (transducer of piezoelectric type or capacitive micromachined ultrasonic transducer called CMUT) to emit an ultrasound signal recognized by the ultrasound imaging device. One alternative consists of using markers having a cavity filled with a fluid containing a contrast product recognized by the ultrasound imaging device. This alternative has the advantage of not requiring an energy source.

To be visible by the endoscopic camera, several solutions can be envisaged. If the marker comprises an energy source, then a light source may also be integrated such as a diode. A simpler solution is to partly coat the marker with a biocompatible paint which will increase the visibility of the marker in the endoscopic image. For improved visibility, the paint may contain fluorophore particles emitting a signal recognized by the endoscopic camera. It is also possible to partly coat the marker with a reflective material.

For a more complete description of the imaging system permitting the merging of endoscopic and ultrasound data in close to real time, with a view to synthesizing an enhanced image, it may be helpful to refer to French patent application FR-07-57158 filed on 24 Aug. 2007.

At all events, it is possible to use any means which in one way or another allow determination of the relative positioning of the instrument and organ.

Different methods can be envisaged to detect and characterize the quality of a detected organ or portion of organ.

Among these methods, two particular general principles underlie the "endoscopic" methods currently being developed and under improvement. The first consists of characterizing the quality of the tissue of the organ subsequent to the detection of characteristic energies emitted by these tissues previously exposed to an appropriate energy source (typically light in several wavelengths). The second consists of coupling the organ, whose quality it is more particularly desired to evaluate, with means to emit a signal which is recognized by the imaging device and characteristic of tissue quality.

Regarding the first approach, and in the area of prostate surgery, the person skilled in the art may for example refer successively to different works. P. Crow et al in "Assessment of fiberoptic near-infrared raman spectroscopy for diagnosis of bladder and prostate cancer", Adult Urology, 2005 (6), report on the use of a Raman spectroscopy system to characterize the benign or malignant nature of prostate tissue (per-surgical prostate samples) with good sensitivity and specificity (respectively 84 and 87). In "Second prize: preliminary experience with the Niris optical coherence tomography system during laparoscopic and robotic prostatectomy", Journal of Urology, 2007 August; 21(8):814-8, the team led by Gill I S et al. reports on the feasibility of characterizing prostate neurovascular bundles using optical imaging of functional Optical Coherence Tomography (OCT) type, in the near infrared. Other approaches can evidently be considered.

Concerning the second approach and again in the area of prostate surgery, the principle is the same as previously presented. A fluorophore is labelled with an antibody specific not to an organ but to an organ quality (cf. example previously described concerning the characterization of the neurovascular bundles).

By collecting these different data on the instrument(s), organ(s) or portion(s) of organ present at the operative site, and on their relative positioning, it is possible to choose a conceptual surgical step in the database which corresponds to the detected surgical step (which corresponds to the surgical step in progress). This choice also allows identification of all past performed surgical steps contained in the database and corresponding to this same conceptual surgical step.

This selection of the conceptual surgical step is made by comparing data in the database with detected data. Data may also be used derived from previously detected surgical steps, so as to fine-tune the choice, but more especially to provide the surgeon with more precise information on the quality of surgery being performed. Knowledge of the surgical operation in progress is also helpful to determine this surgical step, since it can reduce the choice to a limited number of surgery protocols corresponding to said surgical operation. This choice is preferably made in automated fashion but could also be manual based on the surgeon's expertise. Selection of the surgery protocol may also take patient characteristics into account (for example physical condition, age, quality of organ tissues, etc.) which may have an impact on the conducting of the surgical operation.

Once the conceptual surgical step in progress has been determined, it is possible to have knowledge of the surgeon's progress in the procedure, but above all it is possible to compare the surgical step currently in progress with the characteristics of the conceptual surgical step, and optionally with data available on past performed surgical steps corresponding to the surgical operation being performed, and to provide the surgeon with information on his/her own procedure.

This information is essentially intended to guide surgery so that any errors may be corrected. The providing of this information is therefore not necessary if no particular positioning error has been detected and if the surgical step in progress conforms to the recommended past performed surgical step.

However, if a positioning error is detected, i.e. if the surgical step in progress corresponds to an incorrect past performed surgical step, for example if the instrument is positioned in such manner that there is a risk of an undesired movement which may lead to aborting endoscopic surgery, the surgeon should be informed so that the position of the instrument under consideration can be modified, even an indication given on how to proceed.

For each comparison of the surgical step in progress with the selected conceptual surgical step or any past performed surgical step, the information given to the surgeon is both qualitative, since an indication is given on the conformity of procedure, and may also be quantitative in that it may comprise indications on the differences and/or discrepancies with recommendations, and optionally solutions to correct these differences and/or discrepancies.

It is recalled that the database of surgical steps, for each surgical operation, not only stores conceptual surgery protocols, but also a certain number of past performed surgery protocols each corresponding to a succession of past performed surgical steps, and optionally referenced as recommended or incorrect past performed surgical steps. For each surgical operation, at least the recommended past performed surgery protocol is stored, corresponding to ideal surgery, and also one recommended past performed surgery protocol which was conducted under ideal conditions during which no difficulty was encountered and the operation correctly performed. The database also comprises surgical steps characterizing past performed protocols during which problems were encountered, notably due to instrument positioning errors in relation to the organs at the operative site.

For each surgical action by the surgeon, and as regularly as possible and preferably in real time, the database is searched for the corresponding conceptual surgical step on the basis of data detected during the surgical step in progress.

If the information on instruments, organs and their relative positioning allows the conceptual surgical step under consideration to be found in the database, it is possible to act accordingly by providing the surgeon with information if necessary. In this case, the surgical step is effectively related to a particular, known conceptual surgery protocol since the surgical step is contained in the database, and it is therefore possible to give indications to the surgeon on the following steps in the procedure. This information may consist of an indication on the proper conducting of the operation, an indication on subsequent positioning of the instruments, an indication on the difference between the real protocol and the ideal protocol (for example by giving information on the number of instruments present, their relative distance, the time spent in the vicinity of an organ, the speed of surgical movements, etc.) or an alert may be given so that the surgeon stops performing an action (notably if the associated protocol leads to aborting the operation). To define these indications, it is possible to use concepts describing the conceptual surgical step (for example, in this surgical step, the forceps must lie on the left of the prostate).

Should no match with a conceptual surgical step be found in the database from information available on the instruments, organs and their relative positioning, then this should be indicated to the surgeon by an adequate alert. The surgeon must effectively be alerted to the fact that a surgical movement may have harmful consequences for the remainder of the operation. The action in progress is probably different from the action required by the recommended surgery protocol, since no match was found in the database. By different is not necessarily meant that the action may be harmful for the remainder of the operation, but the surgeon should nevertheless be alerted. It is also possible that no match is found with the surgical step in progress subsequent to failed automatic selection in the database (due for example to faulty detections of instruments, organs and/or their relative positions). In this case, it is possible for example to suggest to the surgeon to choose a conceptual surgical step manually, which either corresponds or is at least sufficiently close in order to be able to continue surgery.

The characteristics of the surgical step in progress may also be compared with the characteristics of past performed surgical steps that are stored. This will provide the practitioner with more precise information since surgery in progress is analyzed and compared with previously performed operations; therefore the surgical step in progress can be compared with a very close past performed surgical step, the information on the quality of surgery in progress given to the practitioner then being all the more relevant even quantitative. For example, it is possible to compare an indicator quantifying mean speed of movement of forceps during surgery in progress with the mean speed of movement of this same forceps in past performed operative steps available in the database.

It is to be noted that the database storing the different past performed surgical steps is preferably enriched as and when surgical operations are performed. Therefore a surgical step detected during one operation which does not have any match in the database is recorded, so that it can be found during a subsequent surgical operation, and an indication can be given accordingly to the practitioner.

The database storing the different surgery protocols and surgical steps, with their characteristics, can be enriched by other databases with characteristics on the quality of an organ, or portions of organ, and more generally any type of information which may affect the conducting of surgical procedure. As an example, objectivising ganglion invasion detected and identified per-surgically by an endoscopic imaging system and confirmed if necessary by anatomo-pathological testing, may completely transform conducting of the surgical procedure (conversion of minimal surgery to broader surgery further to the results of extemporaneous anatomo-pathological analysis). It is therefore preferable to store this type of information in the database, so that it is possible for example to select conceptual surgery protocols or surgical steps adapted to the physical condition of the patient.

As indicated above, the information given to the surgeon may assume several forms.

If an indication is to be given to the surgeon on re-positioning of the instruments, an overlay can be used for example over the endoscopic image showing the current position of the instruments and surrounding organs, to display a depiction of the instrument to be re-positioned. This overlay indicates the required position of the instrument to perform the corresponding surgical step under ideal conditions i.e. the required position. The surgeon can then move the instrument under consideration to reposition it in an optimal position in order to follow the ideal surgery protocol. The depiction of the instrument can also be based on a subsequent surgical step in the surgery protocol, with a view to guiding surgery in order to rectify a positioning error.

One alternative or complementary solution consists of displaying a depiction of the surgical step on another viewing system parallel to the real-time display of the operative site, this display indicating to the surgeon a new position to be followed for the instrument relative to the organ. This surgical step may for example correspond to the following surgical step in the surgery protocol, provided it allows the surgeon to rectify movement.

Regarding information on the quality of the organ or organ portions, it is possible for example to display, as an overlay over the endoscopic image, a surface representation of this quality.

Any other solution enabling information to be given to the surgeon on surgery in progress, and how it can be modified if necessary, can be envisaged.

FIGS. 2a to 2d illustrate an example of images which can be visualized by a surgeon during surgery, with the proposed system.

Figure 2A:
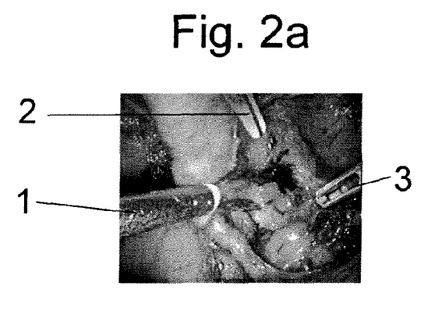
FIGS. 2*a* to 2*d* are endoscopic images of the operative site during surgery under endoscopy, performed with the assistance of the system allowing implementation of the method illustrated in FIG. 1.

This series of images corresponds to the dissection step of the Retzius space in its lateral part as can be seen in FIG. 2a. As can be ascertained, there are three instruments 1, 2, 3 present at the operative site, which entails the presence of two practitioners (in general the surgeon and an assistant).

Figure 2B:
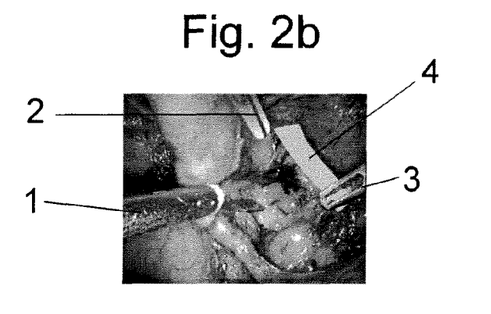

The image in FIG. 2b highlights the organ 4 targeted by the instrument 3 on the right side during this step of the surgery protocol. The instrument 3 should largely bypass the iliac vein so that the vein and the cellulose lymphoid tissues close to it can be folded back, so as to dissect away from the vein. The evidencing of this iliac vein may be made for example using ultrasound imaging means whose data is merged with the data from the endoscopic camera, for the purpose of synthesizing an enhanced image. To do so, the method to merge endoscopic and ultrasound data described above can be used.

This image shown in FIG. 2b is used to determine automatically the instruments present at the operative site, the surrounding organs and their relative positions, so as to identify the corresponding conceptual surgical step and past performed surgical step(s).

Once the conceptual surgical step has been chosen, the comparison between the characteristics of the surgical step in progress and the characteristics of the conceptual surgical step, and optionally with those of corresponding past performed surgical step(s), allows the transmission of information to the practitioner to indicate any incorrect positioning of the instrument 3.

Having regard to the relative positioning of the instruments and organs, the detected surgical step, and the surgery protocol in progress, the database contains information which can be used to predict the following surgical step if the practitioner does not change the positioning of the instruments relative to organs. In the case in hand, if the practitioner continues the surgical step in progress with the positioning of the instruments as in FIG. 2b, there is a risk of an operative incident as in the surgical step illustrated in FIG. 2c. More precisely, if the instrument 3 is not moved, it would retract the iliac vein 4 alone and pull on a small collateral vein which would cause bleeding 5.

Figure 2C:
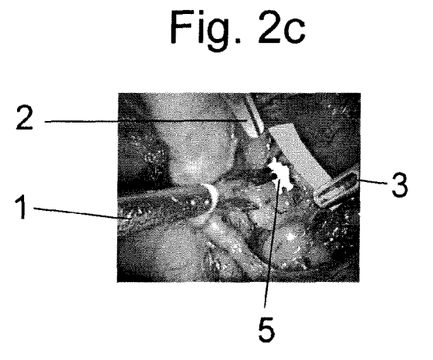
Figure 2D:
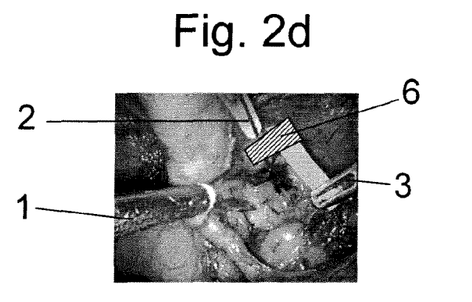

To avoid the incident illustrated in FIG. 2c, information is therefore given to the practitioner in the form of an overlay display 6 of the instrument, at the required position for the proper conducting of the surgical step (see FIG. 2d). This overlaid display guides the practitioner for repositioning of the instrument 3 and thereby avoid a surgical complication.

The surgery analysis method and system described are essentially intended to assist the surgeon in taking decisions during a real operation. This can considerably reduce any errors which may occur during endoscopic surgery, and can notably avoid having to terminate an operation under conventional open surgery on account of an error caused by incorrect positioning of an instrument.

They may also be helpful for surgery followed by tele-monitoring, i.e. when an experienced surgeon remotely monitors a surgical operation being performed by a less experienced surgeon, so that assistance may be given if necessary. Instead of requiring an experienced surgeon to monitor a whole operation, an alert may solely be given if an abnormal surgical step is detected during the operation in progress and/or if the database and expertise of the novice surgeon are not sufficient to solve the identified anomaly.

This method and system may also be used during the practical learning phase, when surgeons train on cadavers or animals. They will then no longer have to wait for retrospective analysis of their performance to detect errors and draw the necessary teachings, since any errors committed will be corrected in real time.

Finally, the method and system described can be used for retrospective analysis of endoscopic surgery just performed by a practitioner. The detection of non-conforming surgical steps during this surgical operation can specifically point to problems which occurred during surgery. This avoids practitioners having to review the entire surgical operation so that they can focus more specifically on the surgical steps considered to be non-conforming.

The reader will appreciate that numerous modifications can be made hereto without materially departing from the novel teachings and advantages described herein. Therefore any such modifications are to be incorporated within the scope of the analysis method and system described for an endoscopic surgical operation.

The invention claimed is:

1. An analysis method for a surgical operation via endoscopy at an operative site in a volume located inside a body, the method comprising:
    a) selecting the surgical operation to be performed;
    b) detecting from an image of the operative site at least one instrument present therein,
    c) detecting from the image of the operative site at least one portion of an organ in the vicinity of the detected instrument,
    d) determining the positioning of the detected instrument relative to the detected organ, so that the detected instrument, the detected portion of organ, and their relative positioning form parameters defining a detected surgical step,
    e) selecting in a database a conceptual surgical step corresponding to the detected surgical step of the selected surgical operation from the detected instrument, the detected portion of organ, and their relative positioning,
    f) comparing the parameters of the detected surgical step with the parameters defining the selected conceptual surgical step to determine the differences between these parameters,
    g) (i) comparing the parameters of the detected surgical step with the parameters of a step consisting of at least one past performed surgical step derived from at least one same surgical operation as the selected surgical operation performed previously from a different patient,
        (ii) wherein said at least one past performed surgical step derived from at least one same previous surgical operation from a different patient is stored in a database with the conceptual surgical steps to make a comparison,
    h) displaying an overlay image on the detected image from an endoscope showing a current position of the detected instrument and the detected organ, to indicate an optimal position of the instrument,
    i) automatically varying in real time the overlay image based at least on step (g); and
    j) providing information on the quality of the detected surgical step on the basis of determined differences.

2. The method of claim 1, wherein the method is applied during the surgical operation to provide real time assistance, and the method further comprises using a computer to automatically display information related to at least two of: (a) a number of the instruments present, (b) a relative distance between the instruments, (c) time spent in a vicinity of the organ, or (d) a speed of surgical movements.

3. The method of claim 1, wherein the method is applied after the surgical operation to permit retrospective analysis of the surgical operation carried out, and the method further comprises using a computer to automatically display information related to at least two of: (a) a number of the instruments present, (b) a relative distance between the instruments, (c) time spent in a vicinity of the organ, or (d) a speed of surgical movements.

4. The method of claim 1, further comprising selecting in the database a surgery protocol comprising a succession of surgical steps with a view to performing a surgical operation, the selected surgery protocol corresponding to the selected surgical operation and to a succession of detected surgical steps.

5. The method of claim 4, wherein the surgery protocol is also selected based on parameters characteristic of the body, which is an animal, and may have an impact on conducting of the surgical operation.

6. The method of claim 4, wherein the information on quality comprises depiction of the required position of the instrument relative to the portion of the organ as per the selected conceptual surgical step and the selected surgery protocol.

7. The method of claim 6, wherein the information on quality comprises depiction of the instrument as the overlay over the detected image of the operative site, showing the required position of the instrument relative to the portion of the organ.

8. The method of claim 4, further comprising selecting in the database a succeeding past performed surgical step which, in the selected surgery protocol, follows after the detected surgical step, and displaying a depiction of the succeeding past performed surgical step.

9. The method of claim 4, wherein the additional information comprises triggering an alert if the last detected surgical step does not allow selection of a conceptual surgical step corresponding to the surgical operation being performed and to the succession of previous surgical steps.

10. The method of claim 1, wherein an endoscopic imaging technique is used for detection of the instrument and/or detection of the portion of the organ.

11. The method of claim 10, wherein, for detection of the portion of the organ, a labelling substance to label the organ is used, the substance containing a fluorescent substance and antibodies specific to the organ, and a camera of the endoscope being adapted for the band of fluorescence wavelengths of the labelling substance.

12. An analysis system for a surgical operation via endoscopy performed at an operative site in a volume located inside a body, comprising:
    a) a database in which conceptual surgical steps and past performed surgical steps comprising surgical steps derived from previous specific surgical operations from a different patient(s) are stored,
    b) at least one detector adapted to detect on an image of the operative site at least one instrument present at the operative site,
    c) the at least one detector adapted to detect at least one organ in the vicinity of the detected instrument,
    d) a computer adapted to determine positioning of the detected instrument relative to the detected organ, e) the database being used to select a conceptual surgical step corresponding to a detected surgical step of the selected surgical operation in relation to the detected instrument, to the detected organ and to their relative positioning, f) the computer being adapted to compare parameters of the detected surgical step with parameters defining the selected conceptual surgical step, and to determine the differences between these parameters, g) the computer being adapted to compare the parameters of the detected surgical step with parameters of past performed surgical steps corresponding to the selected conceptual surgical step, and for fine-tuning the differences ascertained, h) a display adapted to provide information on the quality of the detected surgical step on the basis of determined differences; and i) the display also showing information related to at least one of: (i) a number of the detected instruments present, (ii) a relative distance between the detected instruments, (iii) time spent in a vicinity of the detected organ, or (iv) a speed of surgical movements.

13. The system of claim 12, wherein the database is adapted to store surgery protocols, a surgery protocol being a succession of surgical steps with a view to performing a surgical operation, the system further comprising selecting, in the database, a surgery protocol corresponding to the surgical operation being performed, and to a succession of detected surgical steps.

14. The system of claim 13, wherein the display indicates the required position of the instrument relative to the portion of organ as per the selected conceptual surgical step and the selected surgery protocol in an overlay depiction.

15. The system of claim 12, wherein the information on quality is displayed as a depiction of the instrument as an overlay over an image of the operative site, showing the required position of the instrument relative to the portion of the organ.

16. The system of claim 12, wherein the displayed information includes at least one of: the time spent in the vicinity of the detected organ, or the speed of the surgical movements.

17. The system of claim 12, further comprising an alert being triggered if the last detected surgical step does not allow selection of a conceptual surgical step corresponding to the surgical operation being performed and to the succession of prior surgical steps.

18. An analysis system for a surgical operation via endoscopy performed at an operative site, the system comprising:
   (a) an endoscope camera detecting an image of at least one instrument and at least one organ at the operative site;
   (b) a light source, adjacent to the operative site, used to increase an imaging contrast of at least one of: the organ or the instrument;
   (c) a database including data from previously detected surgical steps on at least one prior patient including previously detected incorrect instrument positions and previously detected ideal instrument positions; and
   (d) an overlay image of the database data displayed over the endoscopic image.

19. The system of claim 18, further comprising a display showing a quantity of the detected instruments.

20. The system of claim 18, further comprising a display showing a relative distance between the detected instruments.

21. The system of claim 18, further comprising a display showing time spent in a vicinity of the detected organ.

22. The system of claim 18, further comprising a display showing movement speed of the surgical instruments.

23. The system of claim 18, wherein the overlay image is automatically varied in real-time based on the detected surgical performance.

24. The system of claim 18, wherein the light source includes a fluorescent substance.

* * * * *